United States Patent [19]

Shaw

[11] Patent Number: 5,788,491
[45] Date of Patent: Aug. 4, 1998

[54] DENTAL FILLING MATRIX BAND RETAINER METHOD

[75] Inventor: Peter D. Shaw, 11096 Red Cedar, San Diego, Calif. 92131

[73] Assignees: Peter D. Shaw; David Kramer, both of Santa Ana, Calif.

[21] Appl. No.: 892,030

[22] Filed: Jul. 14, 1997

[51] Int. Cl.$^6$ ................................................. A61C 5/04
[52] U.S. Cl. ................................................. 433/155
[58] Field of Search ............................ 433/155, 39

[56] References Cited

U.S. PATENT DOCUMENTS

| | | | |
|---|---|---|---|
| 1,165,149 | 12/1915 | Bonnalie | 433/155 |
| 2,232,236 | 2/1941 | Hlavac et al. | 433/155 |
| 2,439,703 | 4/1948 | Tofflemire | 433/155 |
| 2,502,903 | 4/1950 | Tofflemire | 433/155 |
| 2,591,745 | 4/1952 | Tofflemire | 433/155 |
| 2,611,182 | 9/1952 | Tofflemire | 433/155 |
| 2,853,782 | 9/1958 | Gruenwald | 433/155 |
| 3,099,088 | 7/1963 | Ivory, Jr. | 433/155 |
| 3,145,472 | 8/1964 | Tofflemire | 433/155 |
| 4,961,706 | 10/1990 | Jefferies | 433/39 |
| 5,342,197 | 8/1994 | Stein et al. | 433/155 |

*Primary Examiner*—John J. Wilson
*Attorney, Agent, or Firm*—William W. Haefliger

[57] ABSTRACT

A dental matrix retention apparatus which comprises a longitudinally extending frame member, and two laterally extending fingers at an end of the frame member, the fingers being integral with the frame member, each finger having longitudinally spaced primary and secondary sides, there being a finger slot between the fingers and communicating with the primary and secondary sides of the fingers, the fingers projecting in laterally offset relation to a plane defined by the frame member; a holder carried by the longitudinally extending frame member for adjustable longitudinal movement therealong, the holder defining a holder slot, openingly facing the finger secondary sides; a band having a looping section to loop about a tooth, and overlapping sections, the band overlapping sections extending through the finger slot and then directly to the holder slot for retention therein, the band-looping sections extending adjacent the finger primary sides to be tightened toward the primary sides as the holder is adjustably moved longitudinally relative to the fingers.

9 Claims, 2 Drawing Sheets

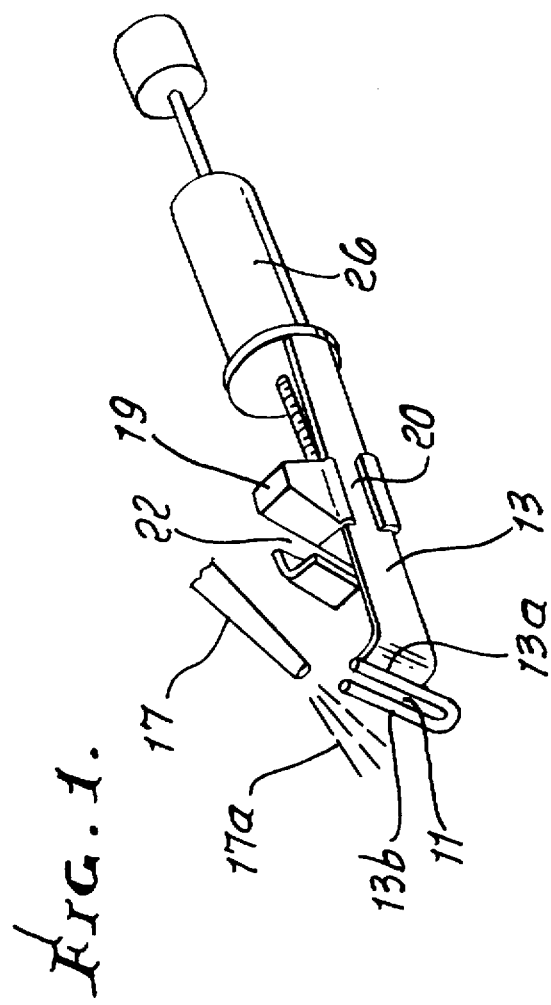
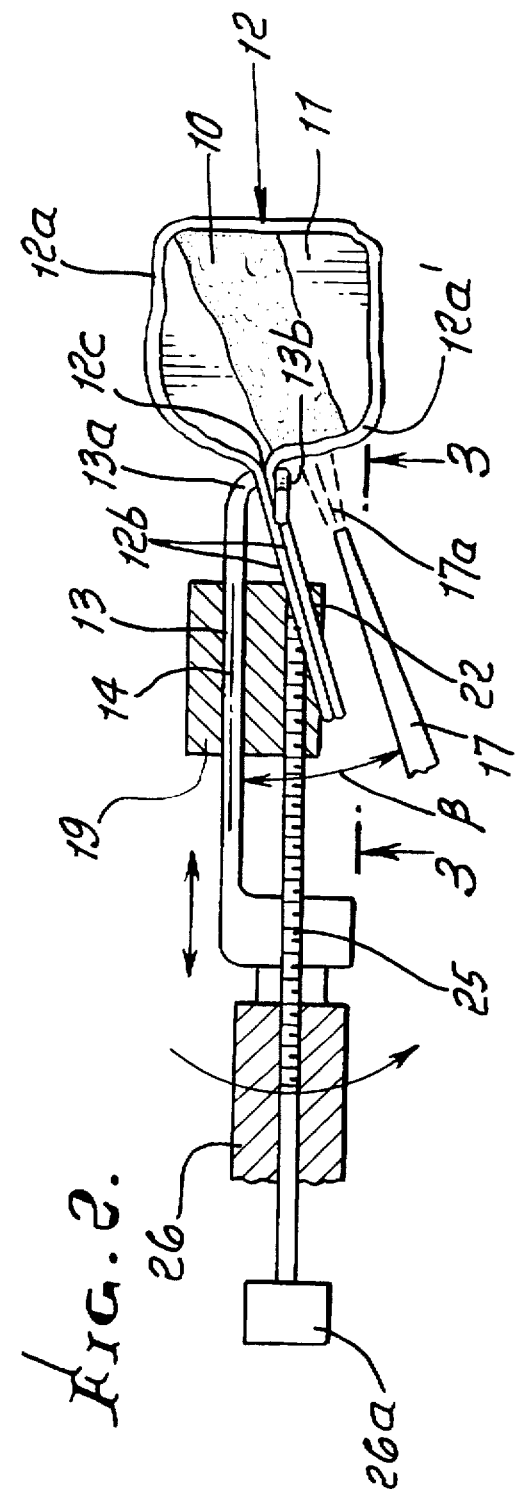

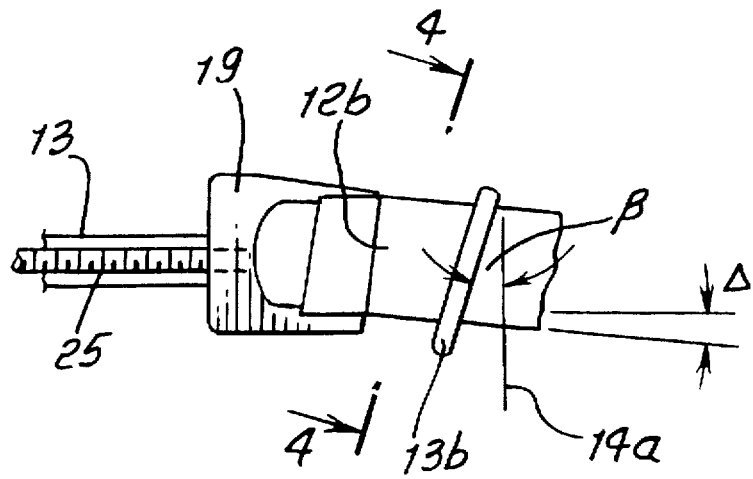
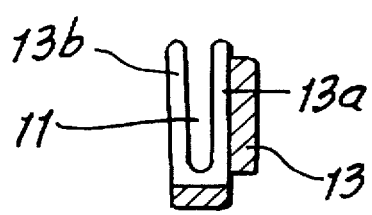
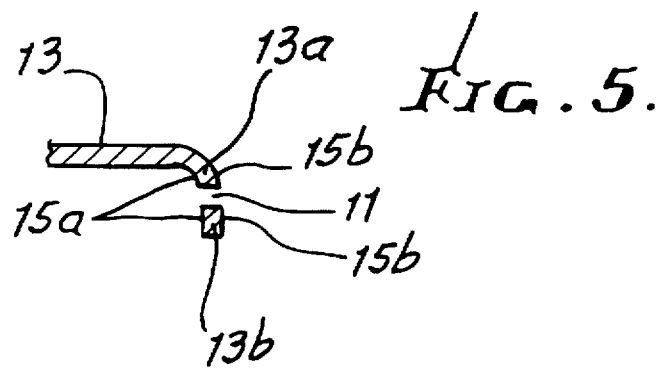

DENTAL FILLING MATRIX BAND RETAINER METHOD

BACKGROUND OF THE INVENTION

This invention relates generally to dental matrix retention apparatus, and more specifically concerns improvements that enhance curing of light curable matrix material filled into a tooth.

Matrix retainers are known, as exemplified in expired U.S. Pat. Nos. 2,502,903 and 2,591,745 to Tofflemire. Such retainer equipment employs a band that is tightened about a tooth into which curable matrix material is filled.

There is need for improvements upon matrix retainer apparatus which enable closer placement or locating of light beam ducting apparatus to light curable filling material in a tooth about which the band is looped. There is also need for simplified retainer apparatus.

SUMMARY OF THE INVENTION

It is a major object of the invention to provide apparatus and method meeting the above needs. Basically, the apparatus provided by the invention comprises:

a) a longitudinally extending frame member, and two laterally extending fingers at an end of the frame member, the fingers being integral with the frame member, each finger having longitudinally spaced primary and secondary sides, there being a finger slot between the fingers and communicating with the primary and secondary sides of the fingers, the fingers projecting in laterally offset relation to a plane defined by the frame member, b) a holder carried by the longitudinally extending frame member for adjustable relative longitudinal movement therealong, the holder defining a holder slot, openingly facing the finger secondary sides, c) a band having a looping section to loop about a tooth, and overlapping sections, the band overlapping sections extending through the finger slot and then directly to the holder slot for retention therein, the band-looping sections extending adjacent the finger primary sides to be tightened toward the primary sides as the holder is adjustably moved longitudinally relative to the fingers.

It is another object of the invention to provide such improved apparatus wherein a substantial portion of the band-looping section projects laterally beyond the fingers to be openly spaced from the holder, whereby a light beam may be directed from a region near the holder toward the band-looping section fitted about a light beam curable filling in a tooth.

A further object includes provision of means for directing the light beam from the region near the holder toward the band-looping section, for effecting curing of the filling.

Yet another object is to provide such apparatus wherein the two spaced fingers are the only spaced fingers carried by the frame, and extend in L-shaped relation to the frame member. In this regard, the finger slot and the holder slot are in substantial alignment.

An additional object is to provide an improved member of using such apparatus, which includes:

d) causing a substantial portion of the band-looping section to project laterally beyond the fingers to be openingly spaced from the holder, e) and directing a light beam from a region near the holder toward the band-looping section fitted about a light curable filling in a tooth.

In this regard, the holder is typically moved relatively along the frame member to effect tightening of the band-looping section against the primary sides of the fingers.

These and other objects and advantages of the invention, as well as the details of an illustrative embodiment, will be more fully understood from the following specification and drawings, in which:

DRAWING DESCRIPTION

FIG. 1 is a perspective view of the apparatus incorporating the invention;

FIG. 2 is an enlarged top plan view of an end portion of the FIG. 1 apparatus, in use;

FIG. 3 is an elevation taken on lines 3—3 of FIG. 2;

FIG. 4 is an enlarged end view of two fingers; and

FIG. 5 is an enlarged fragmentary view of the two fingers.

DETAILED DESCRIPTION

As shown, the apparatus is used to enhance curing of light-curable matrix material 10 filled into a tooth 11, as during dental procedure. For this purpose, a thin band 12 is employed, having a looping portion 12a to loop around the tooth and hold the matrix material in position. The band also has overlapping sections 12b that come together at 12c and are pulled toward two fingers 13a and 13b of a longitudinally extending frame member 13. Those two like fingers are at an end of the member 13, and extend laterally, one above the other in FIG. 2, and in L-shaped relation to the member 13, whereby the fingers project laterally in offset relation to a longitudinal plane 14 defined by member 13. Note the angularity of the fingers in FIG. 3 relative to a plane 14a normal to plane 14. Angle $\beta$ is between 50° and 15°.

Each finger has longitudinally spaced, primary and secondary opposite sides 15a and 15b, as better seen in FIG. 5. A slot 11 is formed between the fingers to pass the band overlapping section 12b, adjacent the locus at which the bands come together from the looping portion 12a, as seen in FIG. 2. Secondary sides 15b of the fingers snugly seat against the pulled adjacent extent of the band-looping portion, whereby a compact fitting relationship is defined, in close relation to a light source 17, for directing a light beam 17a toward the tooth bounded by the band. Such light facilitates rapid curing of the matrix material 10. The band consists of light-passing material, as is known. Note that the light beam is directed at an angle $\alpha$ relative to the longitudinal direction, and closely adjacent finger 13b.

Major extent 12a" of the band-looping portion 12a projects openly laterally in offset relation to the fingers 13a and 13b, for exposure to the light beam. Only two such fingers 13a and 13b are employed, to enable location of the band-looping portion as close as possible to the light source. The parallel edges of band 12b are angled at $\Delta$ relative to the horizontal frame to further facilitate closeness of source 17 to the tooth. Angle $\Delta$ is between 5° and 15°.

Also provided is a holder 19, slidably carried by the frame member 13, for adjustable longitudinal movement therealong. Note the sliding fit at 20 of the holder on the frame member. The holder defines a slot 22, directed openly toward the finger sides 15a. The band overlapping sections 12b extend from slot 11 toward and into slot 22, for retention therein. See for example clamp screw 25 extending in the holder to clamp the received band sections. An adjustment nut 26, rotatable on screw 25, adjustably retracts the holder relative to the frame member to retract the band sections 12b, causing the looping portion of the bands to seat against the sides 15b of the two fingers, as shown, in close relation to the light source. Nut 26a rotates the screw in thread 25a, in holder 19.

Extreme compactness, as provided by the use of only two fingers, as described, is important as respects usage in dental work, where light beam curing of matrix fillings is employed. Note that a substantial portion of the band-looping section projects laterally beyond the fingers to be openingly spaced from the holder, whereby a light beam may be directed from a region near the holder toward the band-looping section fitted about a light curable filling in a tooth.

I claim:

1. In a dental matrix retention method, the steps comprising:

a) providing a longitudinally extending frame member, and two laterally extending fingers at an end of the frame member, the fingers being integral with the frame member, each finger having longitudinally spaced primary and secondary sides, there being a finger slot provided between the fingers and communicating with said primary and secondary sides of the fingers, the fingers projecting in laterally offset relation to a plane defined by the frame member, b) providing a holder carried by the longitudinally extending frame member for adjustable longitudinal movement therealong, the holder defining a holder slot, openingly facing said finger secondary sides, c) providing a band having a looping section to loop about a tooth, and overlapping sections, said band overlapping sections extending through said finger slot and then directly to said holder slot for retention therein, the band-looping sections extending adjacent said finger primary sides to be tightened toward said primary sides as said holder is adjustably moved longitudinally relative to said fingers, d) a substantial portion of said bandlooping section provided to project laterally beyond said fingers to be openly spaced from said holder, and directing a light beam from a region near the holder toward said band-looping section fitted about a light beam curable filling in a tooth.

2. The method of claim 1 including orienting said finger slot and said holder slot to be in substantial alignment.

3. The method of claim 1 including causing said light beam to effect curing of said filling.

4. The method of using dental retention apparatus comprising:

a) a longitudinally extending frame member, and two laterally extending fingers at an end of the frame member, the fingers being integral with the frame member, each finger having longitudinally spaced primary and secondary sides, there being a finger slot between the fingers and communicating with said primary and secondary sides of the fingers, the fingers projecting in laterally offset relation to a plane defined by the frame member, b) a holder carried by the longitudinally extending frame member for adjustable longitudinal movement therealong, the holder defining a holder slot, openingly facing said finger secondary sides, c) and a band having a looping section to loop about a tooth, and overlapping sections, said band overlapping sections extending through said finger slot and then directly to said holder slot for retention therein, the band-looping sections extending adjacent said finger primary sides to be tightened toward said primary sides as said holder is adjustable moved longitudinally relative to said fingers, said method including the steps, d) causing a substantial portion of said band-looping section to project laterally freely beyond said fingers to be openly spaced from said holder.

e) and directing a light beam from a region near the holder toward said projecting band-looping section fitted about a light curable filling in a tooth.

5. The method of claim 4 including providing means to clamp said overlapping sections that extend in said holder slot.

6. The method of claim 4 wherein said two spaced fingers are the only spaced fingers carried by the frame, and orienting said two spaced fingers to extend in L-shaped relation to the frame member.

7. The method of claim 6 wherein said fingers are further oriented to project at an angle $\beta$ relative to a lateral plane normal to the longitudinal direction of said frame member, where angle $\beta$ is between 5° and 15°.

8. The method of claim 4 including moving said holder along said frame member to effect tightening of said band-looping section against said primary sides of said fingers.

9. The method of claim 4 including causing said band-looping section to project at an angle $\Delta$ relative to the longitudinal direction of said frame member, where $\Delta$ is between 5° and 15°.

* * * * *